(12) United States Patent
Crawford

(10) Patent No.: US 7,223,258 B2
(45) Date of Patent: *May 29, 2007

(54) SAFETY SHIELD ASSEMBLY

(75) Inventor: Jamieson W. M. Crawford, New York, NY (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 141 days.

This patent is subject to a terminal disclaimer.

(21) Appl. No.: 10/156,611

(22) Filed: May 24, 2002

(65) Prior Publication Data

US 2003/0220614 A1 Nov. 27, 2003
US 2005/0245879 A9 Nov. 3, 2005

Related U.S. Application Data

(63) Continuation-in-part of application No. 09/378,976, filed on Aug. 23, 1999, now Pat. No. 6,440,104.

(60) Provisional application No. 60/098,282, filed on Aug. 28, 1998.

(51) Int. Cl.
*A61M 5/00* (2006.01)
*A61M 5/32* (2006.01)

(52) U.S. Cl. .................. 604/192; 604/110

(58) Field of Classification Search .......... 604/188, 604/197–199, 192, 110, 272, 263, 181–182, 604/187, 905, 195, 264; 128/919
See application file for complete search history.

(56) References Cited

U.S. PATENT DOCUMENTS

| | | | |
|---|---|---|---|
| 1,779,451 A | 10/1930 | Sponsel | |
| 2,004,050 A | 6/1935 | Kerk | |
| 2,700,385 A | 1/1955 | Ortiz | |
| 2,836,942 A | 6/1958 | Miskel | |
| 2,854,976 A | 10/1958 | Heydrich | |
| 2,953,243 A | 9/1960 | Roehr | |
| 3,021,942 A | 2/1962 | Hamilton | |
| 3,073,307 A | 1/1963 | Stevens | |
| 3,074,542 A | 1/1963 | Myerson et al. | |
| 3,255,873 A | 6/1966 | Speelman | |
| 3,294,231 A | 12/1966 | Vanderbeck | |
| 3,323,523 A | 6/1967 | Scislowicz et al. | |
| 3,329,146 A | 7/1967 | Waldman, Jr. | |
| 3,333,682 A | 8/1967 | Burke | |
| 3,367,488 A | 2/1968 | Hamilton | |
| 3,485,239 A | 12/1969 | Vanderbeck | |
| 3,537,452 A | 11/1970 | Wilks | |
| 3,610,240 A | 10/1971 | Harautuneian | |
| 3,658,061 A | 4/1972 | Hall | |

(Continued)

FOREIGN PATENT DOCUMENTS

GB 1 233 302 5/1971

(Continued)

*Primary Examiner*—Matthew DeSanto
(74) *Attorney, Agent, or Firm*—Mark Lindsey

(57) ABSTRACT

The present invention is a safety shield assembly having a shield and a collar for connecting the shield to a fluid handling device whereby the shield may be pivoted with respect to the collar. Preferably, the safety shield assembly may be used with a needle assembly, an intravenous infusion set a syringe, a catheter or other fluid handling devices or assemblies that contain piercing elements.

20 Claims, 16 Drawing Sheets

U.S. PATENT DOCUMENTS

| | | | |
|---|---|---|---|
| 3,828,775 | A | 8/1974 | Armel |
| 3,890,971 | A | 6/1975 | Leeson et al. |
| 3,904,033 | A | 9/1975 | Haerr |
| 3,934,722 | A | 1/1976 | Goldberg |
| 3,968,876 | A | 7/1976 | Brookfield |
| 4,113,090 | A | 9/1978 | Carstens |
| 4,139,009 | A | 2/1979 | Alvarez |
| 4,175,008 | A | 11/1979 | White |
| 4,300,678 | A | 11/1981 | Gyure et al. |
| RE31,086 | E | 11/1982 | Johnson, Jr. et al. |
| 4,375,849 | A | 3/1983 | Hanifl |
| 4,430,082 | A | 2/1984 | Schwabacher |
| 4,592,744 | A | 6/1986 | Jagger et al. |
| 4,634,428 | A | 1/1987 | Cuu |
| 4,643,722 | A | 2/1987 | Smith, Jr. |
| 4,659,330 | A | 4/1987 | Nelson et al. |
| 4,664,249 | A | 5/1987 | Gheradi |
| 4,664,259 | A | 5/1987 | Landis |
| 4,664,654 | A | 5/1987 | Strauss |
| 4,671,408 | A | 6/1987 | Raines et al. |
| 4,681,567 | A | 7/1987 | Masters et al. |
| 4,695,274 | A | 9/1987 | Fox |
| 4,702,738 | A | 10/1987 | Spencer |
| 4,723,943 | A | 2/1988 | Spencer |
| 4,728,320 | A | 3/1988 | Chen |
| 4,728,321 | A | 3/1988 | Chen |
| 4,731,059 | A | 3/1988 | Wanderer et al. |
| 4,735,311 | A | 4/1988 | Lowe et al. |
| 4,735,618 | A | 4/1988 | Hagen |
| 4,737,144 | A | 4/1988 | Choksi |
| 4,738,663 | A | 4/1988 | Bogan |
| 4,743,233 | A | 5/1988 | Schneider |
| 4,746,008 | A | 5/1988 | Heverly et al. |
| 4,747,836 | A | 5/1988 | Luther |
| 4,747,837 | A | 5/1988 | Hauck |
| 4,772,272 | A | 9/1988 | McFarland |
| 4,778,453 | A | 10/1988 | Lopez |
| 4,781,697 | A | 11/1988 | Slaughter |
| 4,782,841 | A | 11/1988 | Lopez |
| 4,790,828 | A | 12/1988 | Dombrowski et al. |
| 4,793,484 | A | 12/1988 | Schoettle |
| 4,795,432 | A | 1/1989 | Karczmer |
| 4,795,443 | A | 1/1989 | Permenter et al. |
| 4,801,295 | A | 1/1989 | Spencer |
| 4,804,372 | A | 2/1989 | Laico et al. |
| 4,813,426 | A | 3/1989 | Haber et al. |
| 4,816,022 | A | 3/1989 | Poncy |
| 4,816,024 | A | 3/1989 | Sitar et al. |
| 4,819,659 | A | 4/1989 | Sitar |
| 4,820,277 | A | 4/1989 | Norelli |
| 4,826,490 | A | 5/1989 | Byrne et al. |
| 4,826,491 | A | 5/1989 | Schramm |
| 4,838,871 | A | 6/1989 | Luther |
| 4,842,587 | A | 6/1989 | Poncy |
| 4,846,796 | A | 7/1989 | Carrell et al. |
| 4,850,968 | A | 7/1989 | Romano |
| 4,850,976 | A | 7/1989 | Heinrich et al. |
| 4,850,977 | A | 7/1989 | Bayless |
| 4,850,978 | A | 7/1989 | Dudar et al. |
| 4,850,994 | A | 7/1989 | Zerbst et al. |
| 4,850,996 | A | 7/1989 | Cree |
| 4,858,607 | A | 8/1989 | Jordan et al. |
| 4,863,434 | A | 9/1989 | Bayless |
| 4,863,435 | A | 9/1989 | Sturman et al. |
| 4,863,436 | A | 9/1989 | Glick |
| 4,867,746 | A | 9/1989 | Dufresne |
| 4,872,552 | A | 10/1989 | Unger |
| 4,874,383 | A | 10/1989 | McNaughton |
| 4,874,384 | A | 10/1989 | Nunez |
| 4,883,469 | A | 11/1989 | Glazier |
| 4,886,503 | A | 12/1989 | Miller |
| 4,888,001 | A | 12/1989 | Schoenberg |
| 4,892,107 | A | 1/1990 | Haber |
| 4,892,521 | A | 1/1990 | Laico et al. |
| 4,900,309 | A | 2/1990 | Netherton et al. |
| 4,909,791 | A | 3/1990 | Norelli |
| 4,909,792 | A | 3/1990 | Norelli |
| 4,921,096 | A | 5/1990 | McFarlane |
| 4,927,018 | A | 5/1990 | Yang et al. |
| 4,944,397 | A | 7/1990 | Miller |
| 4,966,591 | A | 10/1990 | Yuen |
| 4,976,699 | A | 12/1990 | Gold |
| 4,982,842 | A | 1/1991 | Hollister |
| 5,011,475 | A | 4/1991 | Olson |
| 5,011,479 | A | 4/1991 | Le et al. |
| 5,055,102 | A | 10/1991 | Sitnik |
| 5,078,693 | A | 1/1992 | Shine |
| 5,116,325 | A | 5/1992 | Paterson |
| 5,135,509 | A | 8/1992 | Olliffe |
| 5,139,489 | A | 8/1992 | Hollister |
| 5,151,089 | A | 9/1992 | Kirk, III et al. |
| 5,154,285 | A * | 10/1992 | Hollister ..................... 206/365 |
| 5,188,611 | A | 2/1993 | Orgain |
| 5,197,954 | A | 3/1993 | Cameron |
| 5,207,653 | A | 5/1993 | Janjua et al. |
| 5,232,454 | A | 8/1993 | Hollister |
| 5,232,455 | A | 8/1993 | Hollister |
| 5,242,417 | A | 9/1993 | Paudler |
| 5,277,311 | A | 1/1994 | Hollister |
| 5,312,369 | A | 5/1994 | Arcusin et al. |
| 5,401,251 | A | 3/1995 | Hui |
| 5,405,332 | A | 4/1995 | Opalek |
| 5,423,765 | A | 6/1995 | Hollister |
| 5,462,534 | A | 10/1995 | Debreczeni |
| 5,485,854 | A | 1/1996 | Hollister |
| 5,486,163 | A | 1/1996 | Haynes |
| 5,490,841 | A | 2/1996 | Landis |
| 5,509,907 | A | 4/1996 | Bevilacqua |
| 5,533,984 | A | 7/1996 | Parmigiani |
| 5,584,816 | A | 12/1996 | Gyure et al. |
| 5,599,313 | A | 2/1997 | Gyure et al. |
| 5,599,318 | A | 2/1997 | Sweeney et al. |
| 5,603,699 | A | 2/1997 | Shine |
| 5,632,732 | A | 5/1997 | Szabo et al. |
| 5,643,219 | A | 7/1997 | Burns |
| 5,662,617 | A * | 9/1997 | Odell et al. ................. 604/192 |
| 5,665,075 | A | 9/1997 | Gyure et al. |
| 5,669,889 | A | 9/1997 | Gyure et al. |
| 5,693,022 | A | 12/1997 | Haynes |
| 5,702,369 | A | 12/1997 | Mercereau |
| 5,733,265 | A | 3/1998 | Bachman et al. |
| 5,807,351 | A | 9/1998 | Kashmer |
| 5,836,920 | A | 11/1998 | Robertson |
| 5,885,249 | A | 3/1999 | Irisawa |
| 5,913,846 | A | 6/1999 | Szabo |
| 5,993,426 | A | 11/1999 | Hollister |
| 6,077,253 | A | 6/2000 | Cosme |
| 6,080,137 | A | 6/2000 | Pike |
| 6,120,482 | A | 9/2000 | Szabo |
| 6,139,533 | A | 10/2000 | Xia et al. |
| RE37,110 | E | 3/2001 | Hollister |
| RE37,252 | E | 7/2001 | Hollister |
| 6,298,541 | B1 * | 10/2001 | Newby et al. ................. 29/458 |
| 6,319,232 | B1 | 11/2001 | Kashmer |
| 6,328,713 | B1 | 12/2001 | Hollister |
| 6,334,857 | B1 | 1/2002 | Hollister et al. |
| 6,440,104 | B1 * | 8/2002 | Newby et al. ............... 604/192 |
| 6,648,855 | B2 * | 11/2003 | Crawford et al. ........... 604/110 |
| 6,949,086 | B2 * | 9/2005 | Ferguson et al. ........... 604/198 |

FOREIGN PATENT DOCUMENTS

| | | | |
|---|---|---|---|
| GB | | 2 239 604 | 7/1991 |
| GB | | 2 239 607 | 7/1991 |

| | | | | | | |
|---|---|---|---|---|---|---|
| GB | 2 240 273 | 7/1991 | | WO | WO 91/09639 | 7/1991 |
| GB | 2 240 477 | 8/1991 | | WO | WO 93/016745 | 2/1993 |
| WO | WO 87/07162 | 3/1987 | | WO | WO 0178813 | * 10/2001 |
| WO | WO 90/01348 | 2/1990 | | | | |
| WO | WO 91/09637 | 7/1991 | | | | |
| WO | WO 91/09638 | 7/1991 | | * cited by examiner | | |

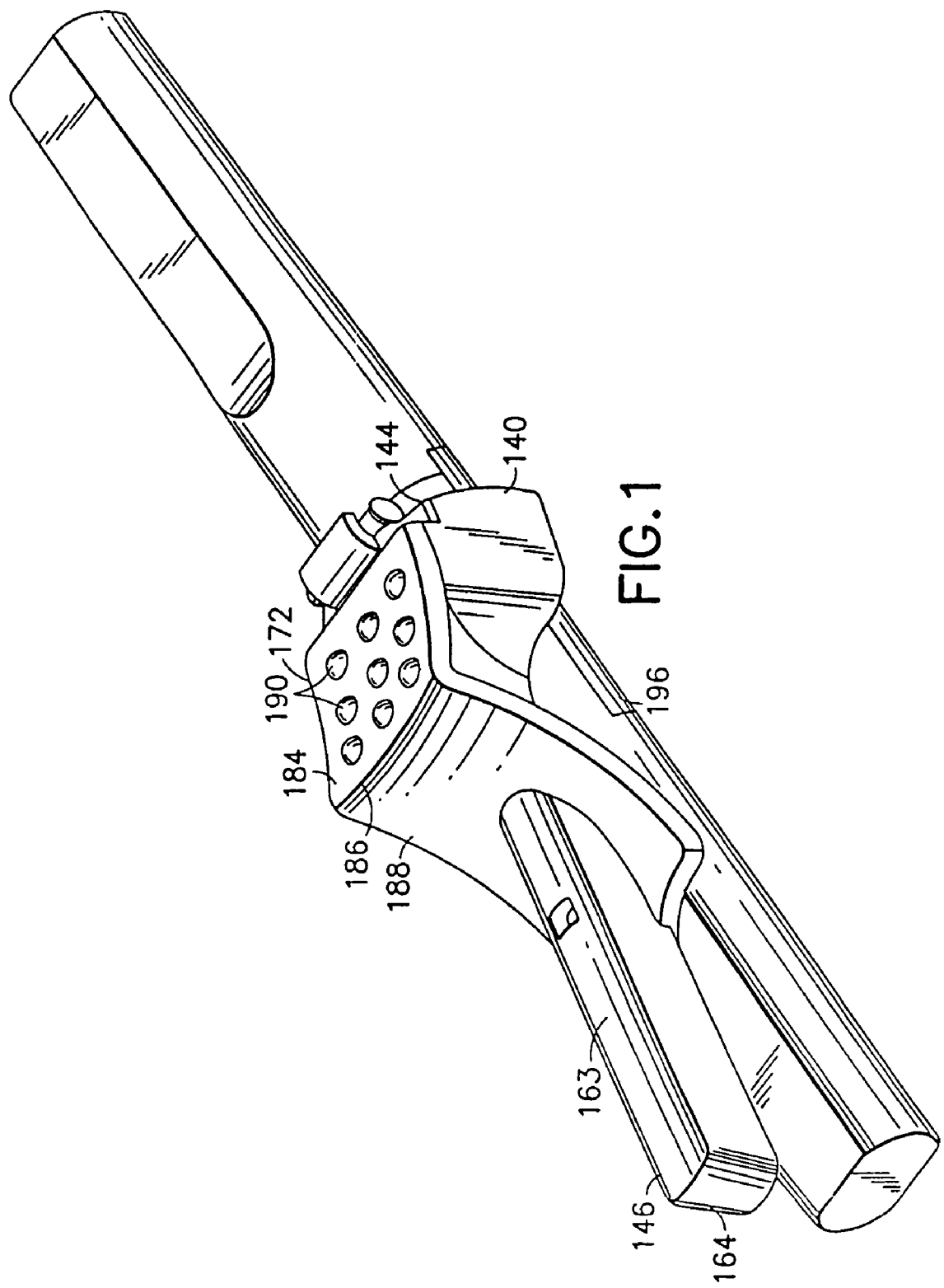

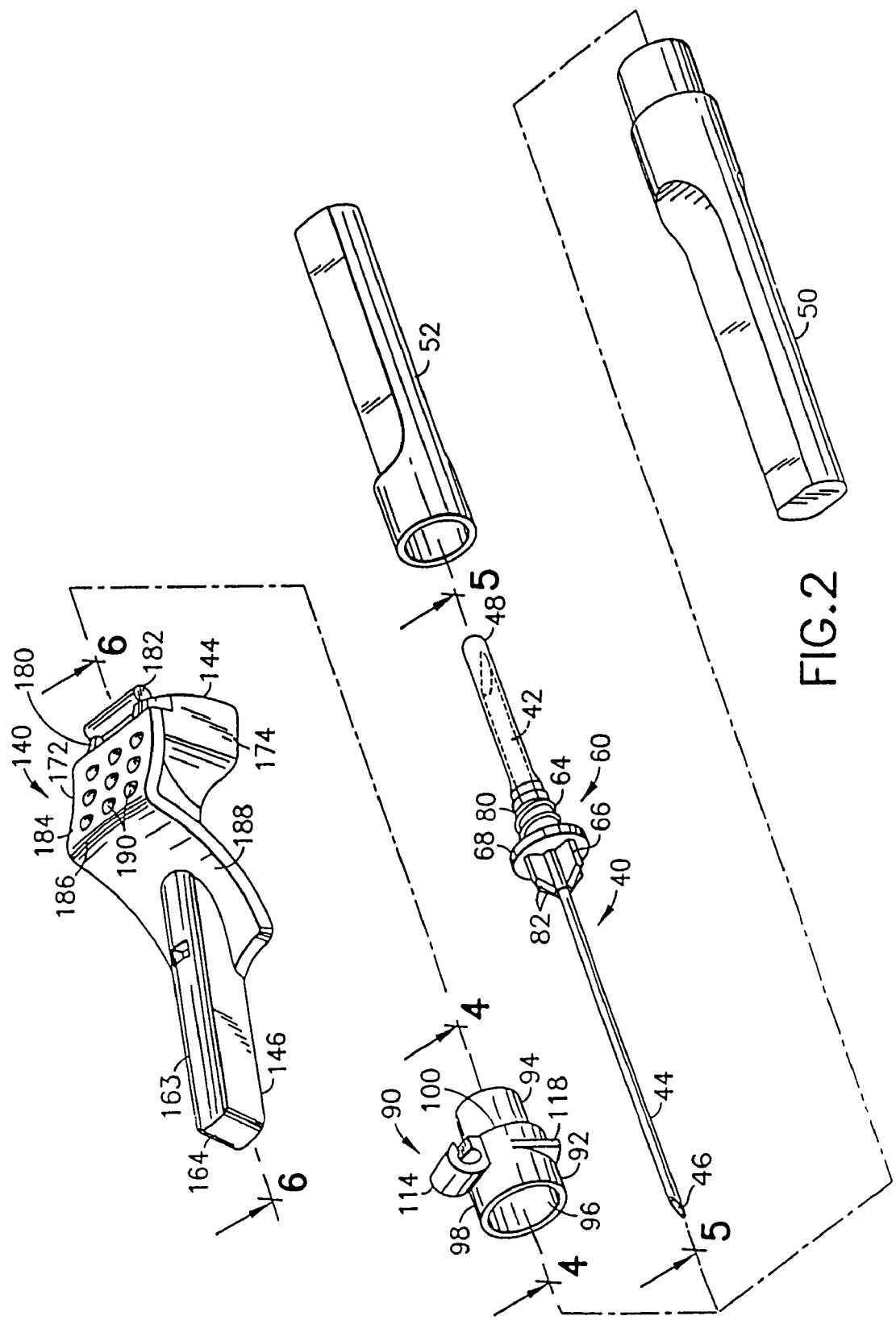

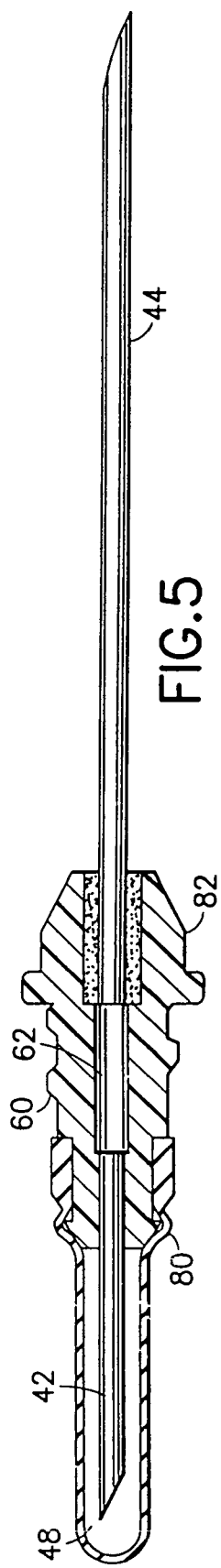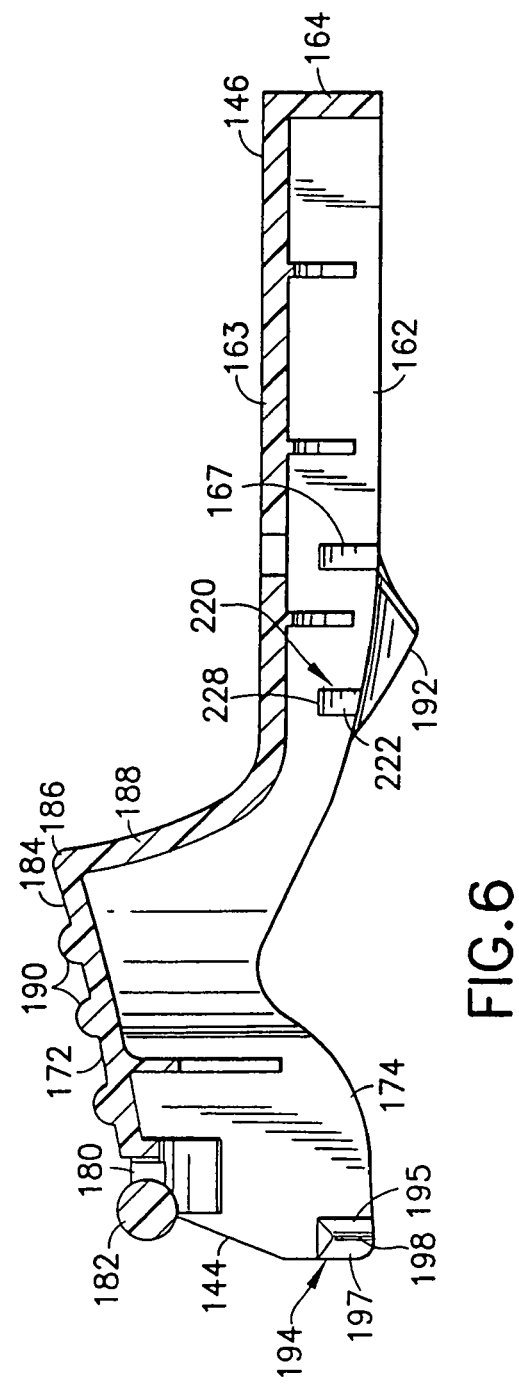

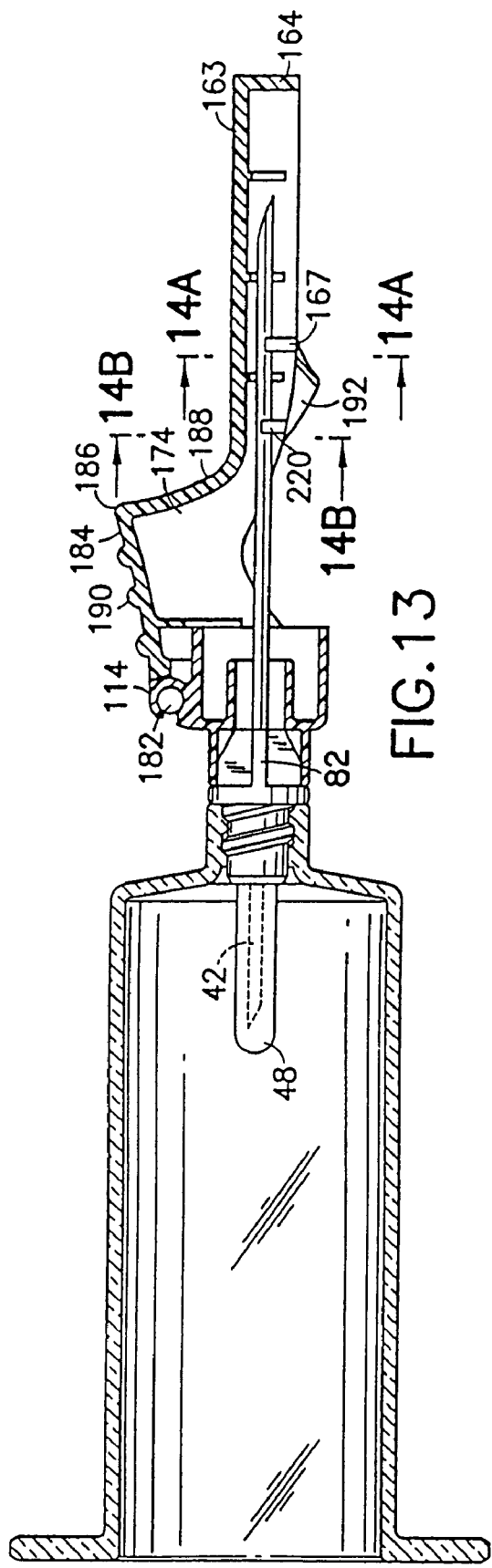
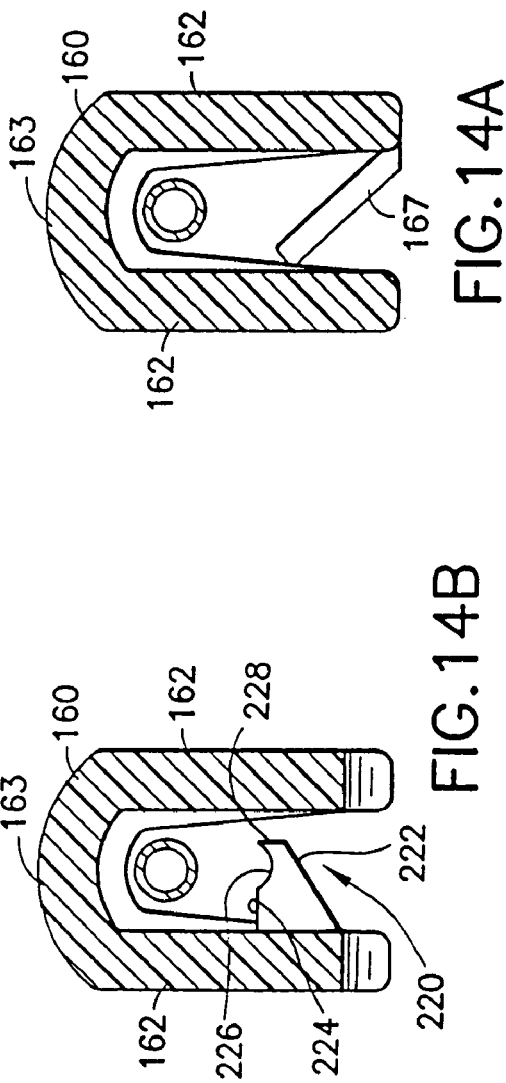
FIG. 13
FIG. 14A
FIG. 14B

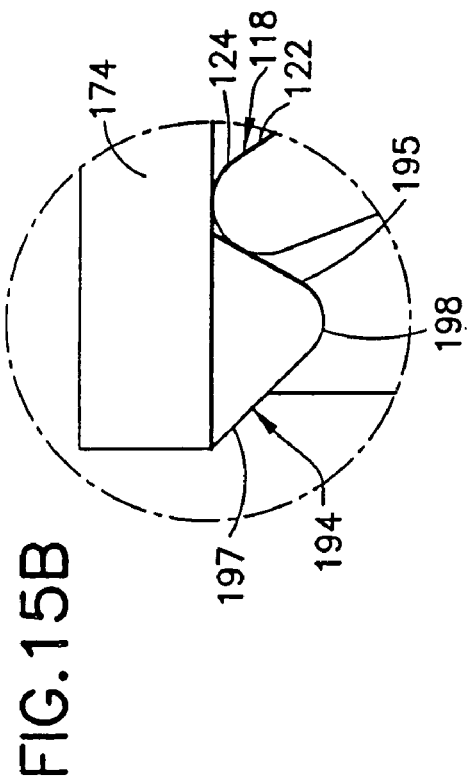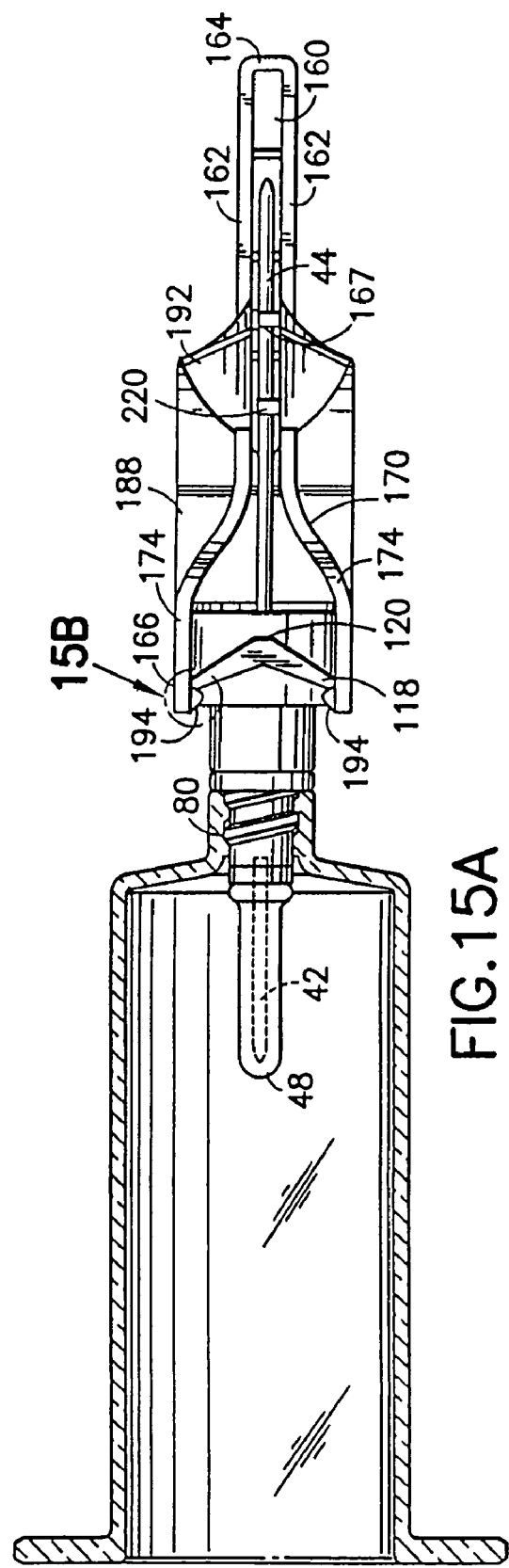

SAFETY SHIELD ASSEMBLY

This application is a continuation-in-part of prior U.S. application Ser. No. 09/378,976, Now U.S. Pat. No. 6,440,104 filed Aug. 23, 1999, which in turn claims the benefit of U.S. Provisional Application No. 60/098,282, filed on Aug. 28, 1998.

1. FIELD OF THE INVENTION

The present invention relates to a shield for a needle and more particularly to a safety shield assembly that may be used in conjunction with a syringe assembly, a hypodermic needle, a needle assembly, a needle assembly with a needle holder, a blood collection needle, a blood collection set, an intravenous infusion set or other fluid handing devices or assemblies that contain piercing elements.

2. BACKGROUND OF THE INVENTION

Disposable medical devices having piercing elements for administering a medication or withdrawing a fluid, such as hypodermic needles, blood collecting needles, fluid handling needles and assemblies thereof, require safe and convenient handling. The piercing elements include, for example, pointed needle cannula or blunt ended cannula.

Safe and convenient handling of disposable medical devices is recognized by those in the medical arts so as to minimize exposure to blood borne pathogens. Safe and convenient handling of disposable medical devices results in the disposal of the medical devices intact.

As a result of this recognition, numerous devices have been developed for shielding needles after use. Many of these devices are somewhat complex and costly. In addition, many of these devices are cumbersome to use in performing procedures. Furthermore, some of the devices are so specific that they preclude use of the device in certain procedures or with certain devices and/or assemblies. For example, some devices employ very short thin needle cannulas. A shield designed to lock near the distal end of one needle cannula might not engage a much shorter needle cannula. Additionally, a shield designed to lock with a wider gauge needle cannula might be more likely to generate a spray upon engaging a much narrower needle cannula. Furthermore, it may be desirable to reduce the force required to effect shielding without reducing the audible and tactile indications of complete shielding.

Therefore, there exists a need for a safety shield assembly: (i) that is manufactured easily; (ii) that is applicable to many devices; (iii) that is simple to use with one hand; (iv) that can be disposed of safely; (v) that does not interfere with normal practices of needle use; (vi) that has tactile features whereby the user may be deterred from contacting the needle, the user may easily orient the needle with the patient and easily actuate and engage the shield assembly; (vii) that has visual features whereby the user may be deterred from contacting the needle, the user may easily orient the needle with the patient and easily actuate and engage the shield assembly; (viii) that is not bulky; (ix) that includes means for minimizing exposure to the user of residual fluid leaking from the needle; and (x) provides minimal exposure to the user because the needle shield is immediately initiated by the user after the needle is withdrawn from the patient's vein.

3. SUMMARY OF THE INVENTION

The present invention is a safety shield assembly that comprises: a shield; means for connecting the shield to a fluid handling device that contains a piercing element, such as needle; means for pivoting the shield away from the needle; and means for securely covering and/or containing the needle within the shield.

Preferably, the shield comprises a rearward end, a forward end, a slot or longitudinal opening for housing the used needle in the forward end, means for securing the needle in the slot, means for guiding the needle into the slot, means for connecting the shield and the fluid handling device, means for guiding the user's fingers to move the shield into various positions, and means for retaining the shield securely over the used needle.

Desirably, the means for connecting the shield to the fluid handling device is a collar. Preferably, the shield is connected movably to a collar which is connected to a fluid handling device.

Preferably, the shield is connected to the collar by a hanger bar that engages with a hook arm on the collar so that the shield may be pivoted with respect to the collar into several positions. It is within the purview of the present invention to include any structure for connecting the shield to the collar so that the shield may be pivoted with respect to the collar. These structures include known mechanical hinges and various linkages, living hinges, or combinations of hinges and linkages.

Most preferably, the shield is connected to the collar by an interference fit between the hanger bar and the hook bar. Therefore, the shield always is oriented in a stable position and will not move forward or backwards unless movement of the shield relative to the hanger bar and the hook bar is initiated by the user.

Alternatively, the shield and collar may be a unitary one-piece structure. The one-piece structure may be obtained by many methods, including molding the shield and the collar as a one-piece unit, thereby eliminating the separate shield and collar during the manufacturing assembly process.

The assembly of the present invention may further comprise tactile and visual means for deterring the user from contacting the needle, providing easy orientation of the needle with the patient and providing the user with a guide for actuation and engagement with the shield.

The assembly of the present invention may further comprise means for minimizing exposure by the user to residual fluid leaking from a used needle. For example, a polymer material, such as a gel, may be located in the shield.

Most desirably, the assembly of the present invention is such that the cooperating parts of the assembly provide the means for the shield to move into a forward position over the needle. Thus, by simple movement of the shield into a forward position over the used needle, the assembly is ready for subsequent disposal. Therefore, the safety shield assembly of the present invention provides minimal exposure of the user to a needle because the shielding is initiated by the user immediately after the needle is withdrawn from the patient's vein.

Desirably, the assembly of the present invention may be used with a syringe assembly, a hypodermic needle, a needle assembly, a needle assembly with a needle holder, a blood collection set, an intravenous infusion set or other fluid handling devices. Preferably, the assembly of the present invention is used with a needle assembly comprising a needle and a hub. Preferably the needle is a conventional double ended needle.

Most preferably, the present invention is used with a needle assembly comprising a hub and a needle connected to the hub whereby the needle comprises a non-patient end and an intravenous end. The collar of the present invention may comprise a hook arm and the shield may be connected movably to the hook arm. Thus the shield may be positioned with respect to the collar and moved easily into several positions.

Preferably, the collar is fitted non-rotatably with the hub of the needle assembly. Additionally, the collar includes cooperating means that mate with reciprocal means on the shield to provide a clear audible and tactile indication of shielding.

The shield preferably includes at least one cannula finger lock for locked engagement with the cannula when the shield is in the second position around the needle cannula. The cannula finger lock preferably projects obliquely from one sidewall of the shield angularly toward the opposed sidewall and the top wall of the shield. The cannula finger lock is dimensioned, disposed and aligned to contact the needle cannula when the shield approaches the second position. Contact between the cannula and the cannula finger lock will cause the cannula finger lock to resiliently deflect toward the sidewall from which the cannula finger lock extends. Sufficient rotation of the shield will cause the needle cannula to pass the cannula finger lock. As a result, the cannula finger lock will resiliently return to or toward its undeflected condition for securely trapping the needle cannula in the shield.

The shield also preferably includes at least one cannula shelf lock. The cannula shelf lock projects substantially rigidly from a sidewall of the shield. The cannula shelf lock may be a generally triangular panel with a lower edge that is inclined closer to the top wall of the shield at further distances from the sidewall on which the shelf lock is disposed. The shelf lock may further include a top edge that extends substantially parallel to the axis of rotation of the shield and/or substantially parallel to the top wall of the shield. The top edge of the shelf lock may include a recess or groove approximately symmetrically between the sidewalls of the shield for trapping the needle cannula. The cannula shelf lock functions differently from the cannula finger lock. In particular, the cannula finger lock is dimensioned and aligned to deflect in response to engagement with the needle cannula. The cannula shelf lock, on the other hand, is dimensioned and aligned to generate deflection of the needle cannula. Thus, the cannula shelf lock will cause the needle cannula to deflect transversely a sufficient distance for the needle cannula to clear the shelf lock. After sufficient rotation, the needle cannula will clear the shelf lock and resiliently return toward an undeflected condition. Thus, the cannula shelf lock will substantially prevent a re-exposure of the used needle cannula.

Preferably, the collar is fitted with the hub of the needle assembly so that the collar cannot rotate around the hub.

Alternatively, the collar and hub may be a unitary one-piece structure. The one piece structure may be accomplished by many methods including molding the collar and the hub as a one-piece unit thereby eliminating the need to separately assemble the collar to the hub during the manufacturing process.

Most preferably, the collar is fitted with the hub of the needle assembly so that the bevel surface or bevel up surface of the intravenous or distal end of the needle faces the same side of the collar when the shield is in the open position. Alignment of the collar, hub, shield and needle with the bevel surface up makes it easier to insert the needle into the patient without manipulating the assembly. The orientation of the intravenous end of the needle with the bevel up assures the user that the needle is properly oriented for use and does not require any manipulation before use. Most notably, the orientation of the shield provides a visual indication to the user of the orientation of the bevel surface of the needle.

Preferably, the shield is capable of pivoting from a first position, where the intravenous end of the needle is exposed and bevel up, to an intermediate position where the needle is partially covered, to a second position where the needle is contained by the shield.

Alternatively, it is within the purview of the present invention that the shield, collar and hub is a unitary one-piece structure. The one-piece structure may be accomplished by many methods including molding the shield, collar and hub as a one-piece unit thereby eliminating the need to separately assemble the shield, collar and hub during the manufacturing process.

It is an advantage of the present invention that the shield covering the used intravenous end of the needle provides easy containment of the used needle. A further advantage of the shield is that it will only move upon initiation by the user.

The assembly of the present invention when used with a fluid handling device is also easily disposable when removed from a conventional needle holder, or other such device.

A notable attribute of the present invention is that it is easily adaptable with many devices. For example, the invention is usable with syringe assemblies, hypodermic needles, needle holders, blood collection needles, blood collection sets, intravenous infusion sets such as catheters or other fluid handling devices or assemblies that contain piercing elements.

Another notable attribute of the present invention is that the tactile and visual features deter the user from touching the needle, allow the user to easily orient the needle with the patient and guide the user to actuate and engage the shield of the assembly.

4. BRIEF DESCRIPTION OF THE DRAWINGS

FIG. 1 is a perspective view of the safety shield assembly of the present invention as connected to a needle assembly and related packaging features.

FIG. 2 is a perspective view of the unassembled pieces of FIG. 1.

FIG. 5 is a cross sectional view of the needle hub as shown in FIG. 2 taken along lines 5—5 thereof.

FIG. 6 is a cross sectional view of the shield of FIG. 2 taken along lines 6—6 thereof.

FIG. 13 is a cross sectional view of the assemblies in use with a conventional needle holder as shown in FIG. 12 taken along lines 13—13 thereof.

FIG. 14A is a cross-sectional view of the assemblies of FIG. 13 taken along lines 14A—14A thereof.

FIG. 14B is a cross-sectional view of the assemblies of FIG. 13 taken along lines 14B—14B thereof.

FIG. 15 is a bottom view of the assemblies as shown in FIG. 11.

5. DETAILED DESCRIPTION OF THE INVENTION

Figure 3A:
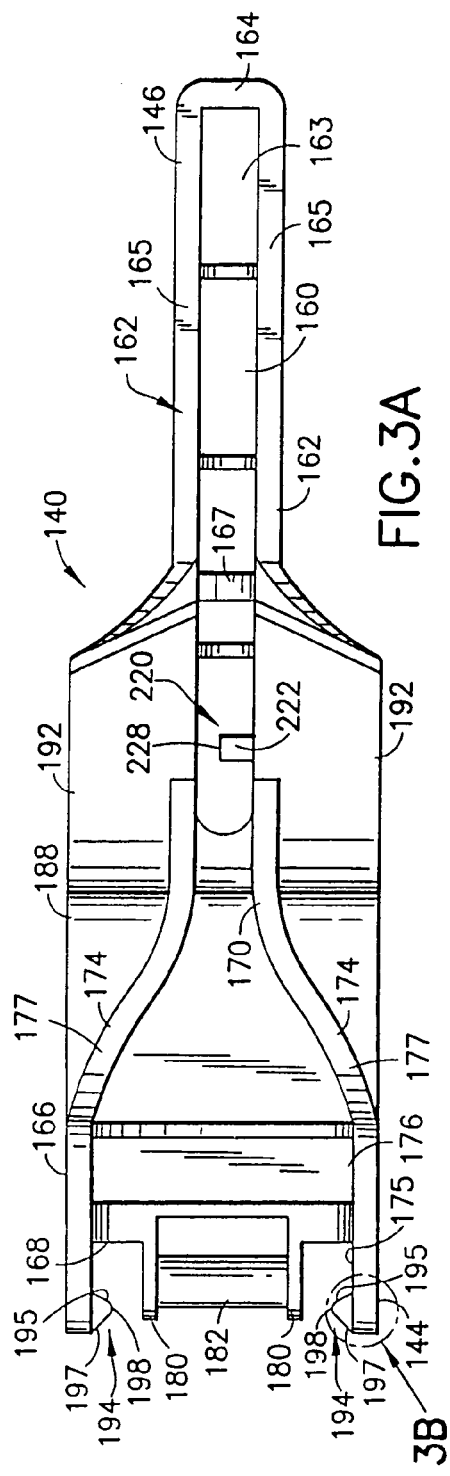
FIG. 3 is a bottom view of the shield as shown in FIG. 2.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIGS. 1 and 2 illustrate a needle assembly with the safety shield assembly of the present invention and the related packaging features. The needle assembly includes a needle 40, a hub 60, packaging features to cover the needle and a label. The safety shield assembly includes a collar 90 and a shield 140.

As shown in FIGS. 2 and 5, needle 40 includes a non-patient end 42, an intravenous end 44 and a passageway 46 extending between the non-patient end and the intravenous end. An elastomeric sleeve 48 covers the non-patient end. A first rigid sleeve 50 covers the intravenous end and a second rigid sleeve 52 covers the non-patient end and the elastomeric sleeve. As shown in FIG. 1, a label 196 may also be applied to the finally assembled parts.

As shown in FIGS. 2 and 5, hub 60 includes a threaded end 64, a ribbed end 66 and passageway 62 extending between the threaded end and the ribbed end. Threaded end 64 and ribbed end 66 are separated by flange 68. Non-patient end 42 of needle 40 extends from threaded end 64 and intravenous end 44 of needle 40 extends from ribbed end 66. Preferably, threaded end 64 comprises male threads 80 for mounting the hub on a conventional needle holder and ribbed end 66 comprises male ribs 82 for connecting the hub and collar 90.

Figure 4:
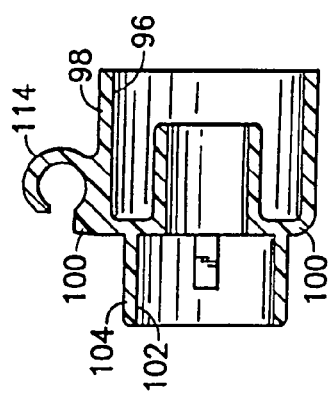
FIG. 4 is a cross sectional view of the collar as shown in of FIG. 2 taken along lines 4—4 thereof.

As shown in FIGS. 2 and 4, collar 90 includes a forward skirt 92 and a rearward skirt 94. Forward skirt 92 is cylindrical and comprises an inner circumferential surface 96 and an outer circumferential surface 98. Forward skirt 92 mates with rearward skirt 94 at a shoulder 100. Rearward skirt 94 is cylindrical and comprises an inner circumferential surface 102 and an outer circumferential surface 104 and extends from shoulder 100 opposite of forward skirt 92. The inner diameter of forward skirt 92 is larger than the inner diameter of rearward skirt 94. Alternatively, the inner diameters for collar 90 can be equal. A hook 114 extends from outer circumferential surface 98 of forward skirt 92. Additionally, detents or protrusions 118 project outwardly from outer circumferential surface 98 of forward skirt 92 at a side opposite hook 114. Protrusions 118 may define a substantially chevron-shape with well defined edges facing toward rearward skirt 94. Alternatively, FIGS. 15A and 15B show that the protrusions may be part of a chevron-shaped projection with a peak 120 pointed toward forward skirt 92 and ramp surfaces 122 that diverge symmetrically from peak 120 toward rearward skirt 94. Ramp surfaces 122 terminate at rounded ends 124 at the outer side and proximal extremes of the chevron-shaped projection. Rounded ends 124 extend continuously into the proximal side of the chevron-shaped projection facing toward rearward skirt 94.

As shown in FIGS. 2 and 6, shield 140 comprises a rearward end 144 and a forward end 146.

Forward end 146 of shield 140 includes a slot or longitudinal opening 160 formed by sidewalls 162 that extend downwardly from top wall 163 and run substantially opposite of one another in parallel along the length of slot 160 towards forward end wall 164. Slot 160 is slightly wider than needle 40. Sidewalls 162 include bottom edges 165 that extend substantially parallel to one another and parallel to top wall 163.

A cannula finger lock 167 is located at one of sidewalls 162 and is configured to secure the used needle. Cannula finger lock 167 extends from a location on a first of the sidewalls 162 adjacent the bottom edge 165 thereof and projects angularly toward the opposed sidewall 162 and toward the top wall 163. The projection of the cannula finger lock 167 from the respective sidewall 162 preferably exceeds half the distance between the respective sidewalls. Cannula first lock 167 is deflectable by the needle when the needle enters slot 160. Once the needle passes the end of cannula finger lock 167, the cannula finger lock moves back to its original position so that the needle is permanently trapped in slot 160 by cannula finger lock 167.

Rearward end 144 of shield 140 defines a collar engaging area 166 that is a continuation of slot 160. Collar engaging area 166 includes a rearward end 168, a forward end 170, a top finger guide area 172, sidewalls 174 that extend downwardly from top finger guide area 172, an underside area 176 dimensioned for surrounding collar 90, and extending arms 180 to support hold hanger bar 182. Sidewalls 174 are spaced apart by a major width adjacent rearward end 168. The major width is selected to enable sidewalls 174 to slide across diametrically opposite side surfaces of forward skirt 92 of collar 90. Sidewalls 174 converge, however, toward forward end 170 to define a minor distance therebetween substantially equal to the distance between sidewalls 162 at forward end 146 of shield 140. Sidewalls 174 include bottom edges 177 that face away from top finger guide area 172. As shown most clearly in FIG. 6, bottom edges 177 curve toward top finger guide area 172 at locations between rearward end 168 and forward end 170 of collar engaging area 166.

Shield 140 further includes a cannula shelf lock 220. Cannula shelf lock 220 is a substantially planar and substantially rigid panel that projects orthogonally from one side wall 174 at a location at or near the interface of forward sidewalls 162 and rearward sidewalls 174. Cannula shelf lock 220 includes a bottom edge extending substantially from bottom edge 177 of sidewall 174 angularly toward top wall 163 and/or top finger guide area 172. Cannula shelf lock 220 further includes a top edge 224 aligned substantially parallel to the axis about which shield 140 rotates. Top edge 224 includes a cylindrically generated concavity 226 generated about an axis extending parallel to top wall 163 and dimensioned to accommodate needle 44. Slanted bottom edge 222 and top edge 224 meet at a corner 228 that is spaced from the opposed sidewall of shield 140 by a distance that exceeds the outside diameter of needle 44.

The extreme rear ends of sidewalls 174 on collar engaging area 166 include rounded ears 194 that project toward one another from opposed inner surfaces 175 of sidewalls 174. Rounded ears 194 are disposed to engage rounded ends 124 of the chevron-shaped projection on collar 90. More particularly, each rounded ear 194 includes a distal surface 195, a proximal surface 197 and a curved surface 198 extending between distal and proximal surfaces 195 and 197. Distal surface 194 is aligned to sidewall 174 an angle of approximately 60° and proximal surface 197 is aligned to sidewall 174 at an angle of approximately 45°. Curved surface 198 extends smoothly and convexly between distal and proximal surfaces 195 and 197. Proximal surfaces 197 of rounded ears 194 will engage detents 118 to deflect sidewalls 174 slightly away from one another as shield 140 approaches the second position. The apex of curved surface 198 on each rounded ear 194 passes the respective detent 118 on collar 90. As a result, sidewalls 174 begin to return resiliently toward an undeflected condition. The resilient return of sidewalls 174 and raked distal surface 195 of ears 194 causes sidewalls 174 to snap against rounded ends 124 of the chevron-shaped projection on collar 90. This snapping action provides a clear audible and tactile indication of shielding and occurs substantially when the used needle is trapped by cannula finger lock 167 and cannula shelf lock 220. The angles of distal and proximal surfaces 195 and 197 of rounded ears 194 affect the performance of shield 140. In particular, a smaller acute angle alignment of proximal face 197 reduces the force required to move shield 140 past rounded ears 194. A larger acute angle proximal surface 197 of rounded ears 194 requires a greater force to move shield 140 toward the second position. Similarly, the angle between distal surface 195 and sidewall 174 affects the acceleration characteristics as shield 140 is propelled toward the second position in response to the resilient return of sidewalls 174. This change in acceleration characteristics affects the audible indication of shielding.

Top finger guide area 172 comprises a first ramp 184 that extends slightly on an upwardly slope from the rearward end of the collar engaging area to a shoulder 186. From shoulder 186 extends a second ramp 188 which slopes downwardly towards top section 163. Most preferably, first ramp 184 comprises touch bumps 190. The touch bumps provide a tactile and visual guide to alert the user that the user's finger has contacted the shield and that the shield is in a defined or controlled position. The touch bumps may be any configuration so long as they extend and are distinct from the top finger guide area. The touch bumps may also be of a distinguishing color as compared to the top finger guide area or the shield.

Second ramp 188 has interior surface 192 for urging the needle toward the center of slot 160 as the shield is being rotated into the closed position. The exterior surfaces are slightly inclined and extending radially from the second ramp. The interior surfaces are especially helpful if the longitudinal axis of the needle is misaligned with respect to the longitudinal axis of the hub.

Extending arms 180 are located at rearward end 168 and at the beginning of top finger area 172 and hold hanger bar 182.

The safety shield assembly and the needle assembly are assembled together whereby needle 40 is connected to hub 60 and sealed with adhesive at the ends of the hub. Hub 60 is then joined with collar 90 by ultra-sonic welding techniques or any other bonding techniques, or mechanical fit, whereby rearward annular skirt 94 of collar 90 mates with ribbed end 66 of the hub. Male ribs 82 of the hub are contained or forced fitted within inner sidewall 102 of rearward annular skirt 94 of collar 90. The collar is aligned with the intravenous end of the needle whereby the hook arm is aligned with the bevel up of the needle. Then rigid sleeve 50 is force fitted into inner side wall 96 of forward skirt 92 of collar 90 to cover the needle. Thereafter, shield 140 is connected to collar 90 whereby hanger bar 182 is force fitted into hook member 114 whereby slot 160 faces rigid sleeve 50. Most preferably, the shield is connected to the collar by a force fit or interference fit between the hanger bar and the hook bar. Therefore, the shield is always oriented in a stable position and will not move unless movement of the shield is positively initiated by the user. To assemble the last piece, shield 140 is moved towards rigid sleeve 50 and second rigid sleeve 52 is force fitted onto outer sidewall 104 of rearward skirt 94 of collar 90.

In addition, a label 196 may be applied to the finally assembled parts. The label may be used to provide tamper resistance of the parts, so that they are not reused.

Figure 9:
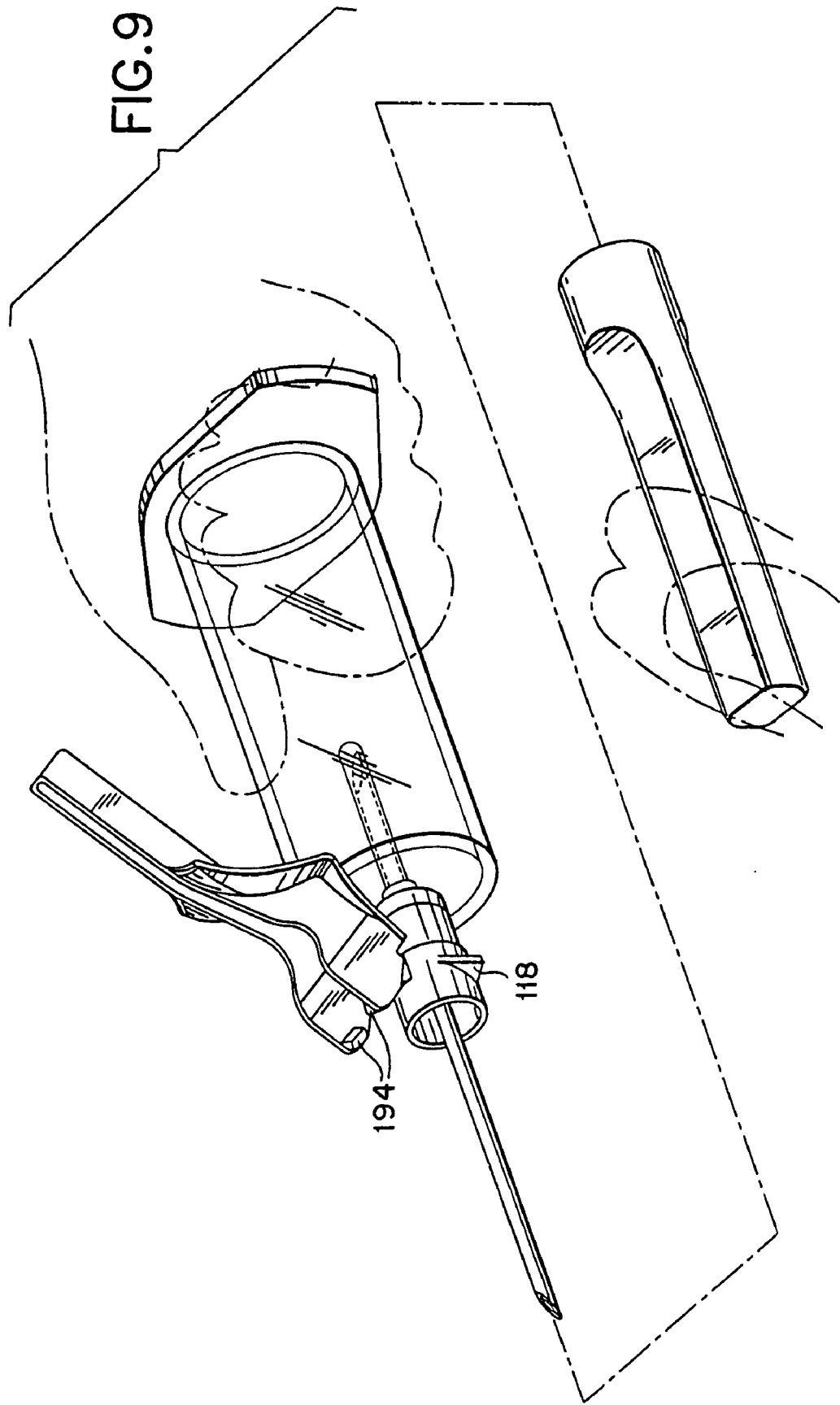
Figure 10:
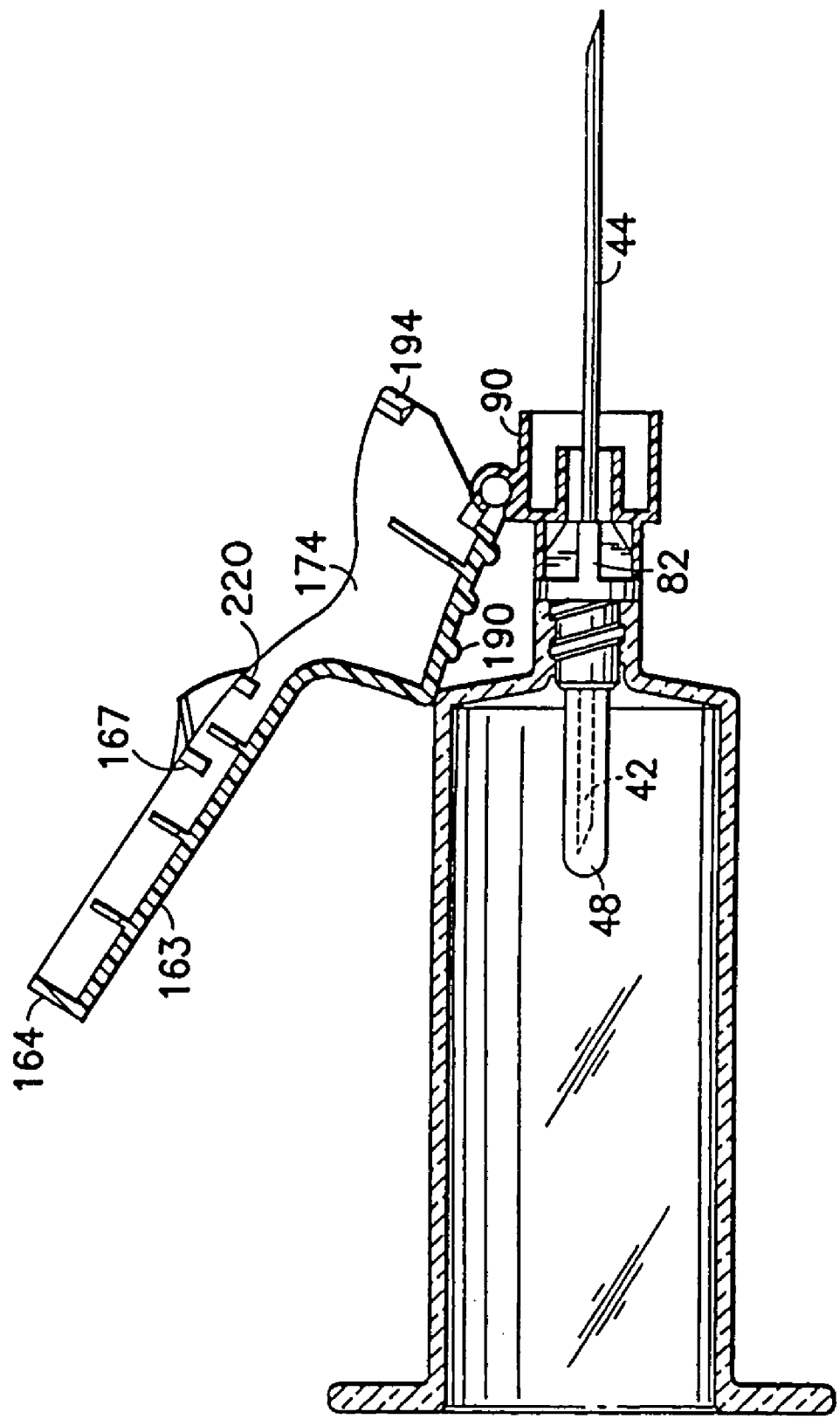
Figure 11:
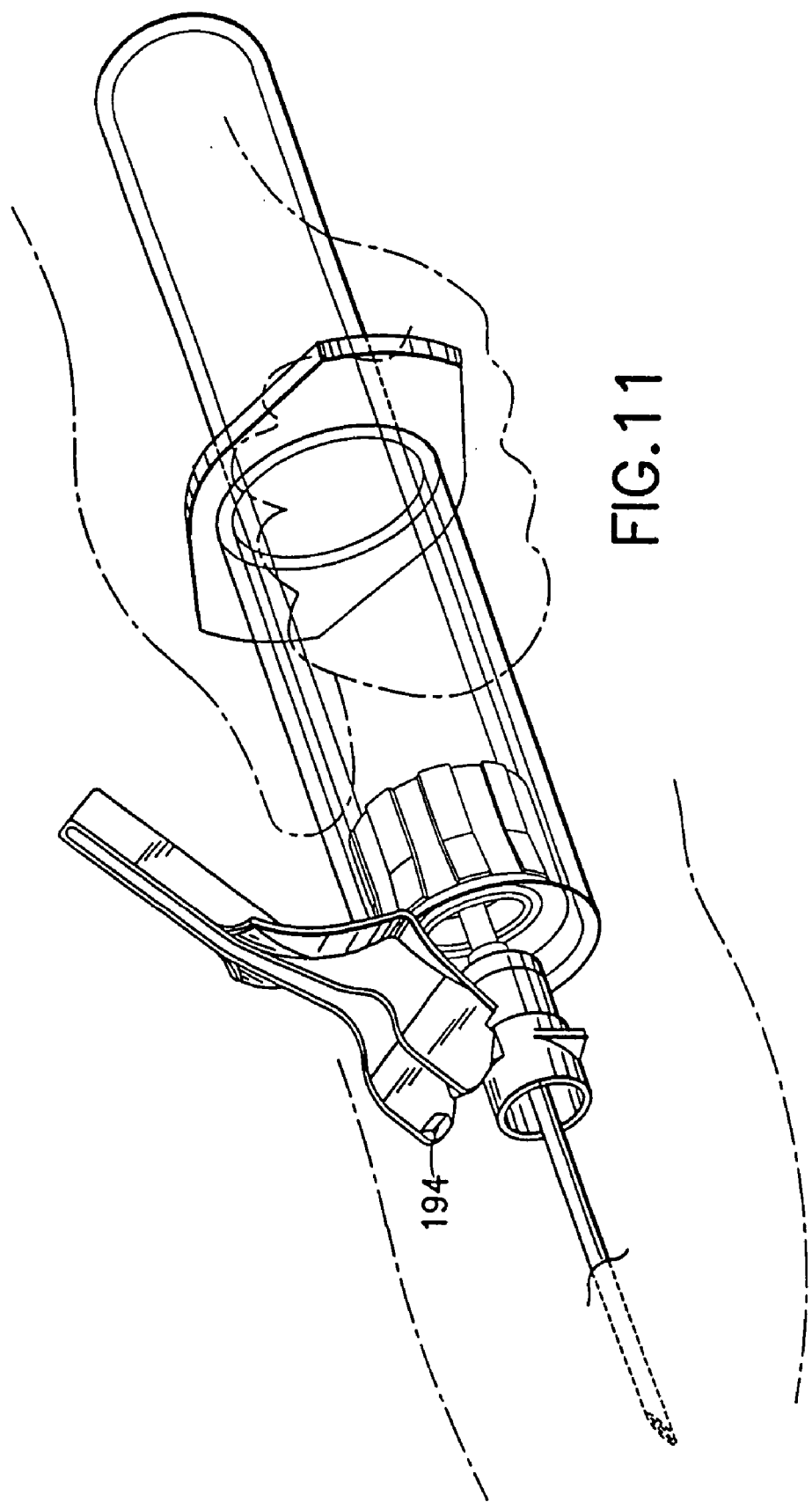
Figure 12:
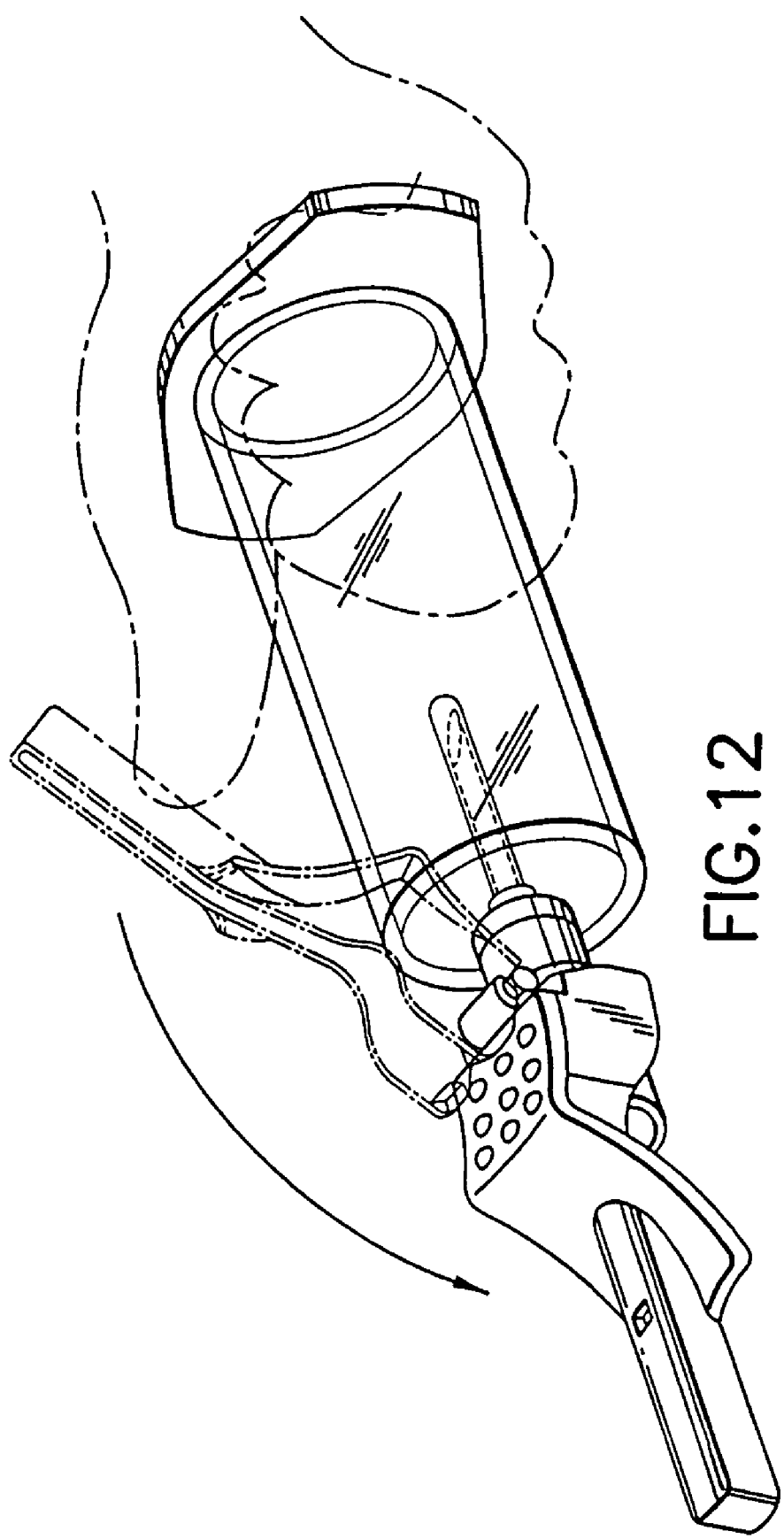

In use, as shown in FIGS. 7–15, the non-patient needle shield is removed and then a needle holder is screwed onto the hub of the needle. As specifically shown in FIGS. 8 and 12 the shield is then rotated back by the user towards the needle holder. Then as shown in FIG. 9, the intravenous needle shield is removed from covering the intravenous needle. Then as shown in FIG. 10, a venipuncture is conducted whereby the intravenous end of the needle is inserted into a vein of a patient and an evacuated tube having a closure is inserted into the needle holder. Then as shown in FIGS. 11 and 13, when the venipuncture is complete the user easily rotates the shield from the open position towards the intravenous needle to an intermediate position and then the user pushes on the shield at the top finger guide area to move the shield into a second position whereby the needle is trapped in the longitudinal opening. More particularly, needle 44 contacts cannula finger lock 167 and cannula shelf lock 220. The engagement of needle 44 with cannula finger lock 167 causes cannula finger lock 167 to deflect toward top wall and toward the sidewall 162 from which cannula finger lock 167 projects. Simultaneously, sloped bottom edge 222 of cannula shelf lock 220 will cause needle 44 to deflect. Sufficient rotation of shield 140 will cause needle 44 to pass both cannula finger lock 167 and cannula shelf lock 220. As a result, cannula finger lock 167 will return resiliently to an undeflected condition and needle 44 will return resiliently to an undeflected condition. Thus, needle 44 will be trapped above cannula finger lock 167 and above cannula shelf lock 220. Additionally, needle 44 will be retained securely in concave region 226 of cannula shelf lock 220. The combination of cannula finger lock 167 and cannula shelf lock 220 can provide more secure protection than a single cannula finger lock. More particularly, a cannula finger lock provides a secure trapping of needle 44, albeit with relatively low resistance to a forced attempt to intentionally re-expose needle 44. On the other hand, shelf lock 220 provides somewhat less effective trapping than cannula finger lock 167 in that a transverse shifting for the shield could bypass a cannula shelf lock that was used alone. However, a cannula shelf lock provides much more secure resistance to a forcible attempt to rotate shield 140 back to its initial position. Thus, the cannula finger lock 167 and cannula shelf lock 220 cooperate to provide significantly enhanced trapping and resistance to re-exposure of cannula 44.

Needle 44 is contained within shield 140 as the shield is pivoted into the second position. More particularly, proximal surfaces 197 of rounded ears 194 move over rounded ends 124 of the chevron-shaped projection on collar 90 and cause sidewalls 174 to deflect away from one another. The angularly aligned proximal faces 197 of rounded ears 194 ensures easy movement of shield 140. Additionally, the resiliency of sidewalls 174 and the angular alignment of distal surface 195 of ears 194 causes shield 140 to be accelerated into the second position. This accelerated movement of shield 140 helps to generate a clear audible and tactile indication of shielding.

Figure 16:
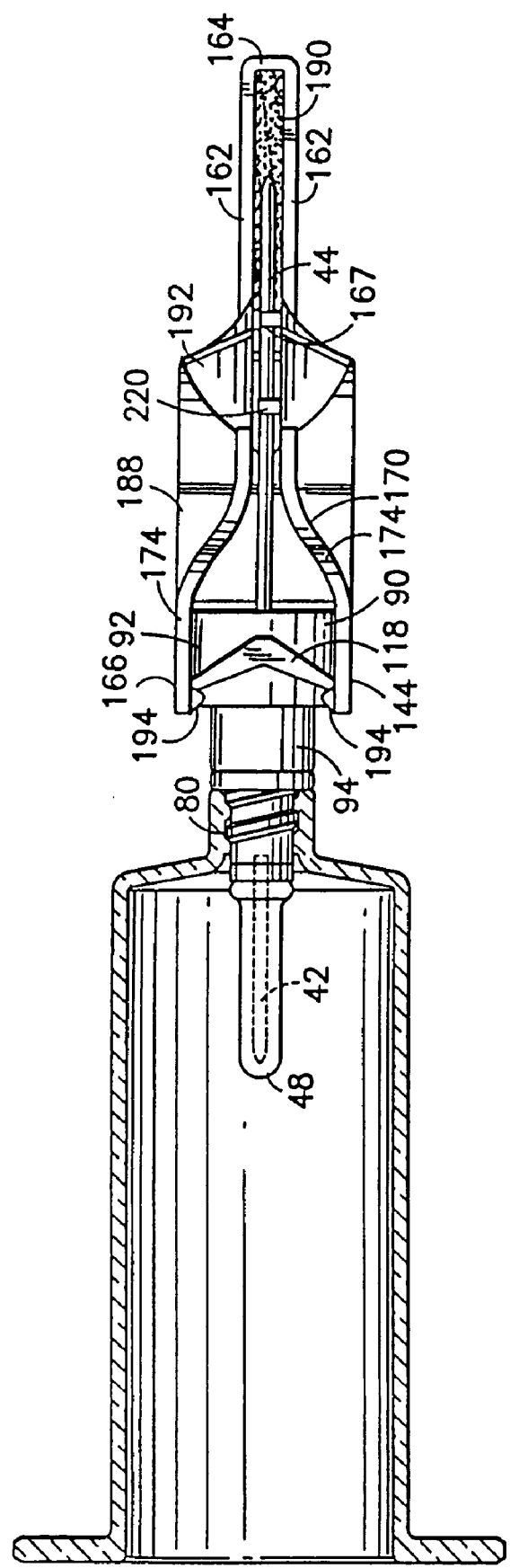
FIG. 16 illustrates an additional embodiment of the present invention, whereby a gel material is located in the shield as shown in a bottom view of the assemblies of FIG. 11.

Alternatively as shown in FIG. 16, a gel material 190 is located in shield 140 so that when the needle snaps past cannula finger lock 167 and cannula shelf lock 220 it will come to rest in gel material 190. The gel material will contain any residual fluid that may be on the needle. Simultaneously, rounded ears or projections 198 move over rounded ends 124 of chevron-shaped projection. This causes sidewalls 174 to deflect away from one another and then to snap back into engagement with collar 90 to provide a clear audible and tactile indication of complete shielding.

Figure 3B:
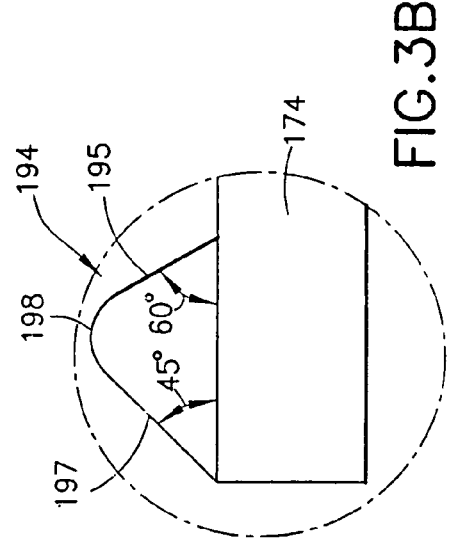
Figure 7:
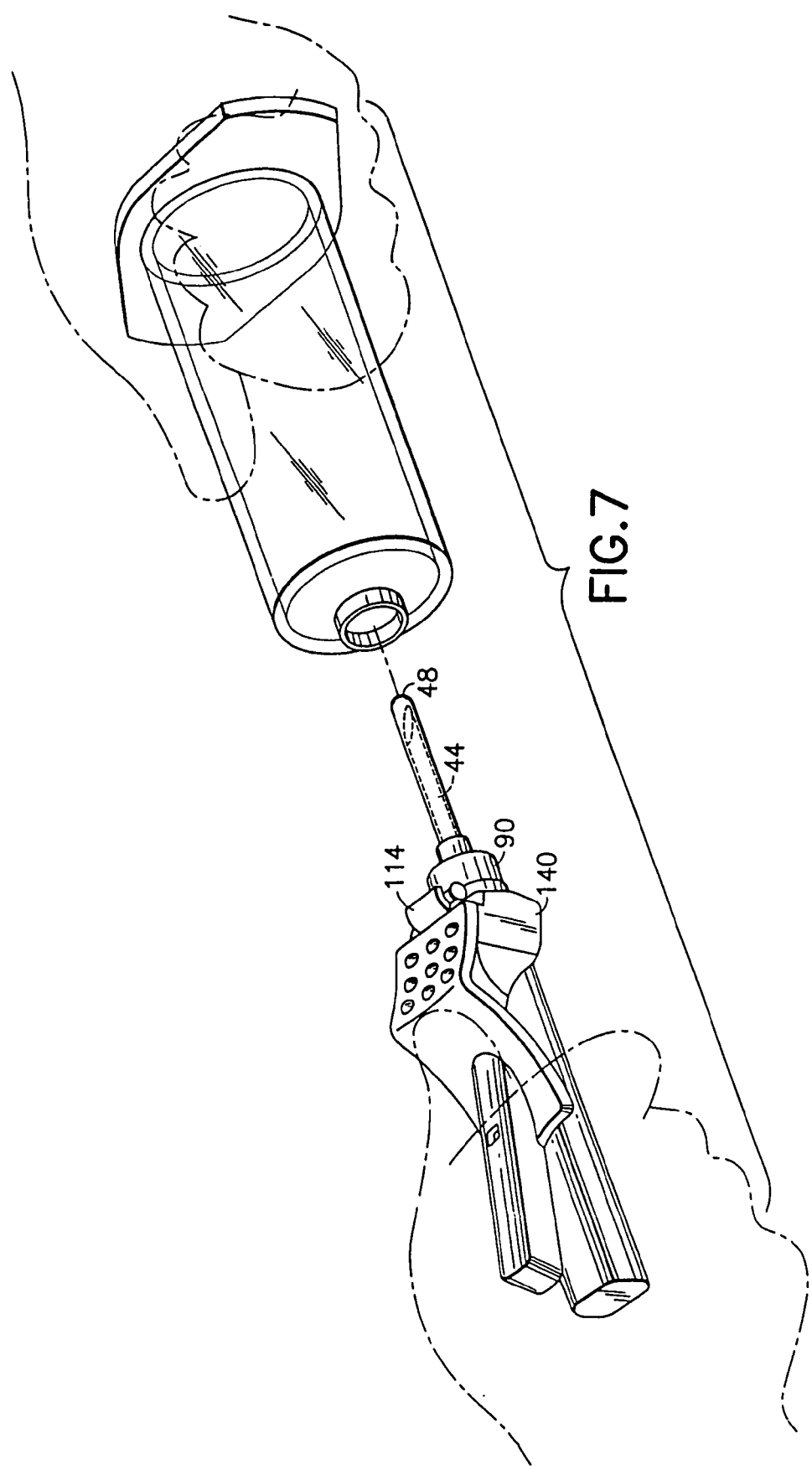
FIGS. 7–12 illustrate the use of the safety shield assembly with the needle assembly of FIG. 1 with a conventional needle holder.
Figure 8:
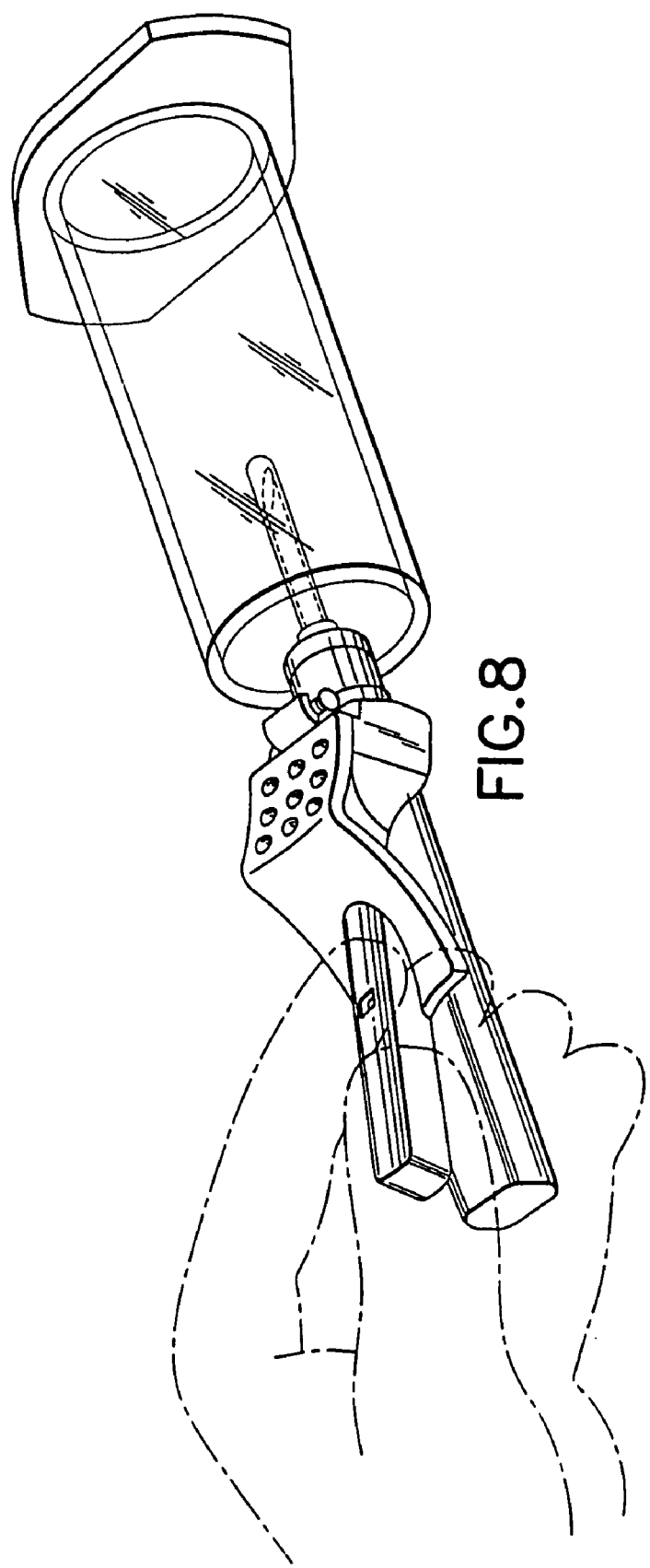
Figure 17:
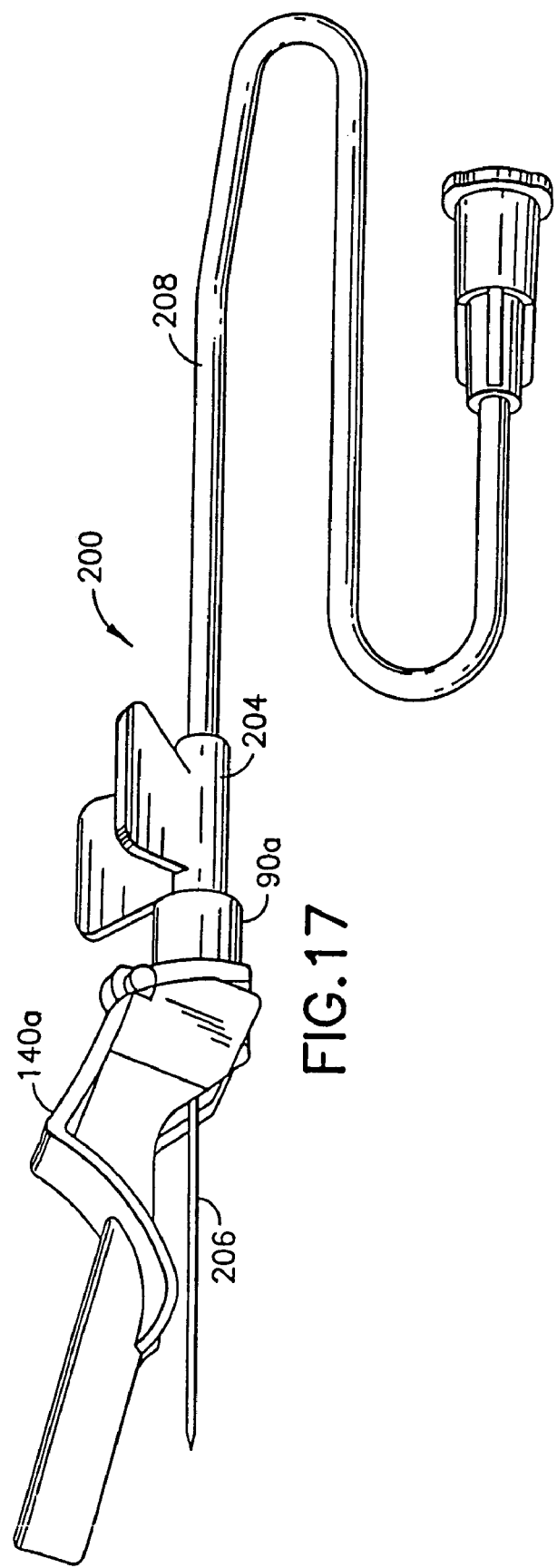
FIG. 17 is a perspective view of an additional embodiment of the present invention in use with a blood collection set.
Figure 18:
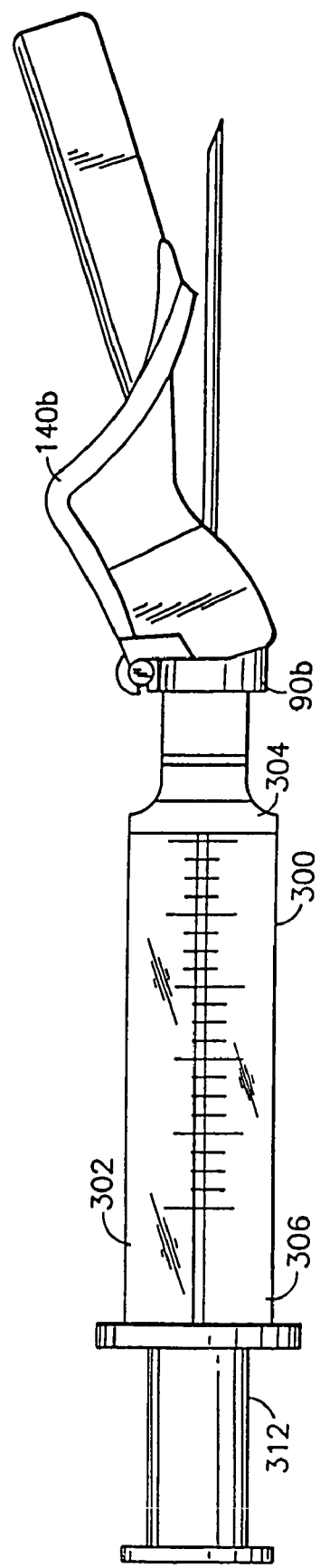
FIG. 18 is a perspective view of an additional embodiment of the present invention in use with a syringe.
Figure 19:
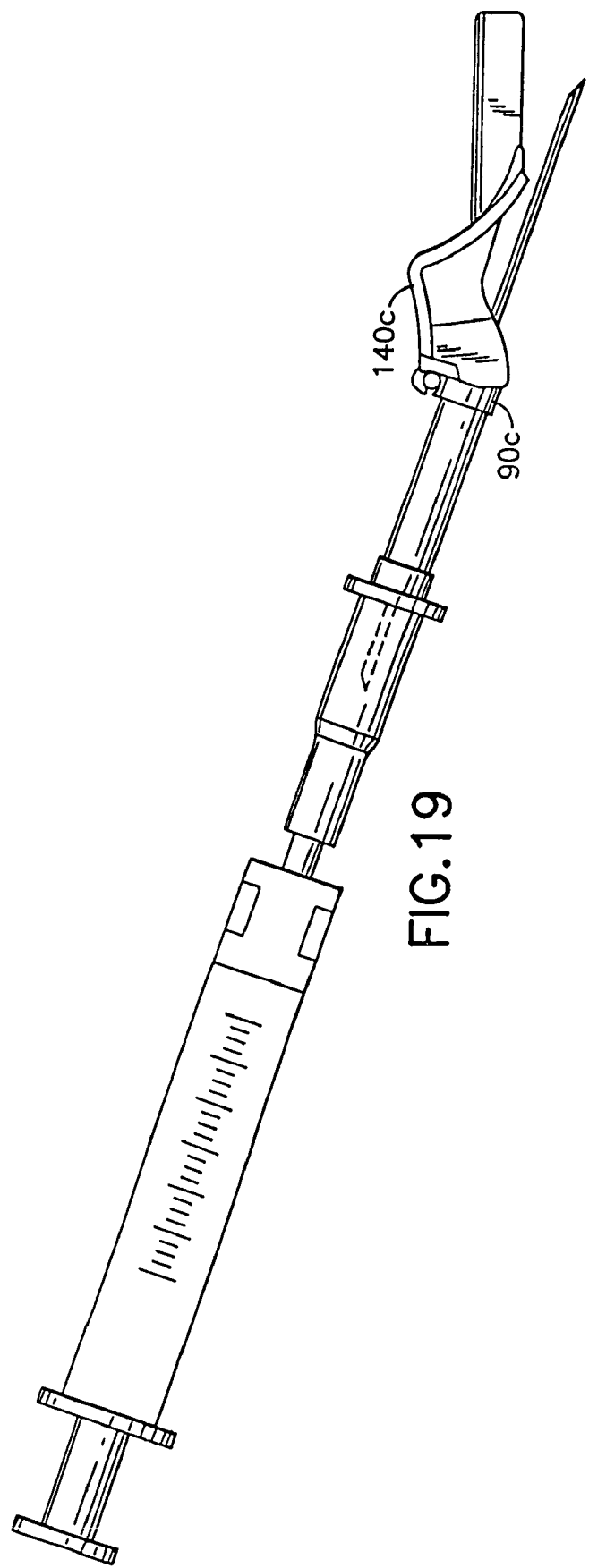
FIG. 19 is a perspective view of an additional embodiment of the present invention in use with a catheter.

FIGS. 17, 18, and 19 are further embodiments of the invention that may include components which are substantially identical to the components of FIGS. 1–3. Accordingly, similar components performing similar functions will be numbered identically to those components of FIGS. 1–3, except that a suffix "a" will be used to identify those similar components in FIG. 17, a suffix "b" will be used to identify those similar components in FIG. 18 and a suffix "c" will be used to identify those similar components in FIG. 19.

Alternatively, the safety shield assembly of the present invention may be used in conjunction with a conventional intravenous (IV) infusion set, as illustrated in FIG. 17.

For purposes of illustration, shield 140a and collar 90a are connected to a conventional IV infusion set, 200, or butterfly structure comprising a needle body with a needle hub 204 extending from the forward end of the needle body and a needle 206 embedded in hub 204. Extending from the rearward end of the needle body is flexible tubing 208 which is conventional and utilized to allow the user to manipulate the structure and to connect it subsequently to supplies of infusion liquids or for the return of collected blood if the arrangement is being used to collect blood.

Infusion set 200 further comprises flexible wings 210 attached to and projecting outwardly from needle hub 204.

Alternatively, the safety shield assembly of the present invention may be used in conjunction with a syringe, as illustrated in FIG. 18.

For purposes of illustration, shield 140b and collar 90b are connected to a conventional hypodermic syringe 300 comprising a syringe barrel 302 having a distal end 304 a proximal end 306 and a plunger 312.

Alternatively, the present invention may be used in conjunction with a catheter as illustrated in FIG. 19.

The shield and collar of the safety shield assembly of the present invention are comprised of moldable parts which can be mass produced from a variety of materials including, for example, polyethylene, polyvinyl chloride, polystyrene or polyethylene and the like. Materials will be selected which will provide the proper covering and support for the structure of the invention in its use, but which will provide also a degree of resiliency for the purpose of providing the cooperative movement relative to the shield and the collar of the assembly.

The illustrated embodiments show certain preferred combinations of features of the disclosed invention. However, certain of those features may be omitted or modified without departing from the scope of the invention as defined by the appended claims. For example, the ends of the chevron-shaped projection can be made less rounded than illustrated in the attached figures to alter the acceleration of the side walls of the shield to an undeflected condition after the rounded ears pass over the chevron-shaped projection. Similarly, the illustrated combination of rounded ears on the shield and a chevron-shaped projection with rounded ends can be used to achieve the desired audible and tactile indications of complete shielding without the above-described shelf lock. Thus, audible and tactile indications of shielding may be achieved by the illustrated chevron-shaped projection and the illustrated rounded ears, while retention of the shield around the needle may be achieved entirely by one or more cannula finger locks.

What is claimed is:

1. A safety needle assembly comprising
a needle hub with proximal and distal ends and
a passage extending between said ends,
a needle cannula mounted to said passage of said needle hub and having a pointed distal end projecting beyond said distal end of said hub,
a shield having proximal and distal ends, said proximal end of said shield being hingedly mounted to said hub for rotation from a first position where said shield is spaced from said needle cannula to a second position where said shield substantially surrounds said needle cannula, said shield comprising
a top wall and opposed first and second sidewalls extending from said top wall, said sidewall having bottom edges remote from said top wall,
a resiliently deflectable cannula finger lock projecting from said first sidewall angularly toward said top wall, and
a substantially rigid cannula shelf lock projecting from one of said sidewalls in a direction toward the opposed sidewall, said cannula shelf lock having a bottom edge sloped toward said top wall and a flat top edge spaced from said top wall such that said bottom and top edges intersect at a corner, wherein said top edge of said cannula shelf lock comprises a concave region facing said top wall for trapping said needle cannula, whereby the cannula finger lock deflects during rotation of said shield toward said second position for trapping said needle cannula, and whereby said cannula shelf lock generates deflection of said needle cannula during said rotation of said shield to said second position, such that said needle cannula is trapped below said top wall and above said cannula finger lock and said cannula shelf lock.

2. The safety needle assembly of claim 1, wherein said cannula shelf lock projects from said first sidewall to said second sidewall.

3. The safety needle assembly of claim 2, wherein the needle cannula defines an outside diameter, said cannula shelf lock being spaced from said second side wall of said shield by a distance greater than said outside diameter of said needle cannula.

4. The safety needle assembly of claim 3, wherein said top edge of said cannula shelf lock is substantially parallel to said top wall of said shield.

5. The safety needle assembly of claim 4, wherein said shield is hingedly mounted to said hub for rotation about an axis, said top edge of said cannula shelf lock being substantially parallel to said axis.

6. The safety needle assembly of claim 5, wherein said cannula shelf lock is substantially planar and substantially orthogonal to said first sidewall.

7. The safety shield assembly of claim 6, wherein said needle hub comprises an inner tubular portion securely mounted to said needle cannula and an outer collar securely mounted over said inner tubular portion, said shield being hingedly mounted to said collar of said hub.

8. The safety needle assembly of claim 7, wherein said needle cannula includes a proximal end, said needle cannula extending entirely through said passage of said hub such that said proximal end of said needle cannula projects proximally beyond said proximal end of said hub.

9. The safety needle assembly of claim 8, further comprising an elastomeric sleeve mounted over said proximal end of said needle cannula and securely engaged to said proximal end of said hub.

10. The safety needle assembly of claim 6, wherein said shield is unitarily formed from a plastic material.

11. The safety needle assembly of claim 1, further comprising detents formed externally on said hub and rounded ears formed on said shield for engaging said detents when said shield is in said second position, said rounded ears and said detents providing audible and tactile indication of said shield reaching said second position.

12. The safety needle assembly of claim 11, wherein said detents comprise two spaced apart detents disposed at locations on said hub substantially opposite said hinged connection of said shield to said hub.

13. The safety needle assembly of claim 12, wherein said rounded ears are formed on inwardly facing surfaces of said sidewalls of said shield.

14. The safety needle assembly of claim 13, wherein said rounded ears are disposed to pass over said detents as said shield is rotated into said second position.

15. The safety needle assembly of claim 14, wherein said rounded ears are dimensioned to require deflection of said sidewalls away from one another as said shield is rotated into said second position and as said rounded ears move over said detents.

16. The safety needle assembly of claim 11, wherein each said rounded ear comprises a proximal face aligned to said respective sidewall at an acute angle, a distal face aligned to said respective side wall at an acute angle and a curved surface extending between said proximal and distal faces.

17. The safety needle assembly of claim 16, wherein said distal face of each said ear is aligned to said respective sidewall at an angle of approximately 60 degrees.

18. The safety needle assembly of claim 11, wherein said detents are firmed on a chevron-shaped projection on said hub.

19. The safety needle assembly of claim 1, wherein said concave region defines a cylindrically generated edge aligned and configured for engaging an outer circumferential surface of said needle cannula.

20. A safety needle assembly comprising
a needle hub with proximal and distal ends and
a passage extending between said ends,
a chevron-shaped projection formed externally on said hub, said chevron-shaped projection including a central point facing distally on said hub and
a pair of rounded ends facing proximally on said hub,
a needle cannula mounted to said passage of said needle hub and having a pointed distal end projecting beyond said distal end of said hub,
a shield having proximal and distal ends, said proximal end of said shield being hingedly mounted to said hub for rotation from a first position where said shield is spaced from said needle cannula to a second position where said shield substantially surrounds said needle cannula, said shield comprising
a top wall and opposed first and second sidewalls extending from said top wall,
a resiliently deflectable cannula finger lock projecting from said first sidewall angularly toward said top wall,
a substantially rigid cannula shelf lock projecting from one of said sidewalls in a direction toward the opposed sidewall, said cannula shelf lock having a bottom edge sloped toward said top wall and a flat top edge spaced from said top wall such that said bottom and top edges intersect at a corner, wherein said top edge of said cannula shelf lock comprises a concave region facing said top wall for trapping said needle cannula,
rounded ears formed on said shield for engaging said rounded proximal ends of said chevron-shaped projection when said shield is rotated toward said second position,
whereby said cannula finger lock latch deflects during rotation of said shield toward said second position, and whereby said cannula shelf lock generates deflection of said needle cannula during said rotation of said shield to said second position, such that said needle cannula is trapped below said top wall and above said cannula finger lock and said cannula shelf lock, said rounded ears and said rounded proximal ends of said chevron-shaped projection providing audible and tactile indication of said shield reaching said second position.

* * * * *